United States Patent [19]

Koreyasu et al.

[11] Patent Number: 5,348,705
[45] Date of Patent: Sep. 20, 1994

[54] AUTOMATIC CLINICAL SAMPLE DISPENSING SYSTEM

[75] Inventors: Toshiyuki Koreyasu, Tokikawa; Shoji Maruyama, Kawagoe, both of Japan

[73] Assignee: B.M.L., Inc., Tokyo, Japan

[21] Appl. No.: 51,615

[22] Filed: Apr. 23, 1993

Related U.S. Application Data

[62] Division of Ser. No. 913,527, Jul. 15, 1992.

[30] Foreign Application Priority Data

Apr. 10, 1992 [JP] Japan ................... 4-118161

[51] Int. Cl.$^5$ ............................ G01N 37/00
[52] U.S. Cl. ........................ 422/67; 422/65; 422/65; 422/100; 436/49; 436/55; 436/47; 436/48
[58] Field of Search ............ 422/65, 63, 67, 68.1, 422/99, 100, 102, 104; 436/43, 47, 48, 50, 55, 49

[56] References Cited

U.S. PATENT DOCUMENTS

| | | | |
|---|---|---|---|
| 4,133,642 | 1/1979 | Nosaka et al. | 422/67 |
| 4,459,265 | 7/1984 | Berglund | 422/64 |
| 4,675,162 | 6/1987 | Sakamaki et al. | 422/65 |
| 4,727,033 | 2/1988 | Hijikata et al. | 436/69 |
| 4,751,186 | 6/1988 | Baisch et al. | 436/47 |
| 5,008,082 | 4/1991 | Shaw | 422/65 |
| 5,096,670 | 3/1992 | Harris et al. | 422/65 |
| 5,128,105 | 7/1992 | Berthold et al. | 422/104 |
| 5,176,880 | 1/1993 | Iwasaki et al. | 422/63 |

Primary Examiner—James C. Housel
Assistant Examiner—Long V. Le
Attorney, Agent, or Firm—Nixon & Vanderhye

[57] ABSTRACT

Sample numbers, which are encoded information about samples including a body fluid and contained in original containers, are affixed to the original containers. The test system memorizes the sample number including a rack number attached to each original container rack and coordinates of each original container in the original container rack. Then, it determines whether or not a sample in the original containers should be dispensed in each dispensing container set in the dispensing container rack using the pre-dispensing sample positional information including a rack number attached to each original container rack and coordinates of each original container in the original container rack, as a key. Based on the determination, an automatic dispensing machine dispense a to-be-dispensed sample into an associated one of the dispensing containers, and memorizes the sample numbers in association with post-dispensing sample positional information including a rack number affixed to the dispensing container rack where sample-dispensed dispensing containers are set and coordinates of the dispensing containers in the dispensing container rack. The sample number may have a mark obtained by simplifying the sample number in accordance with a predetermined regularity so that operators can find sample easily.

1 Claim, 6 Drawing Sheets

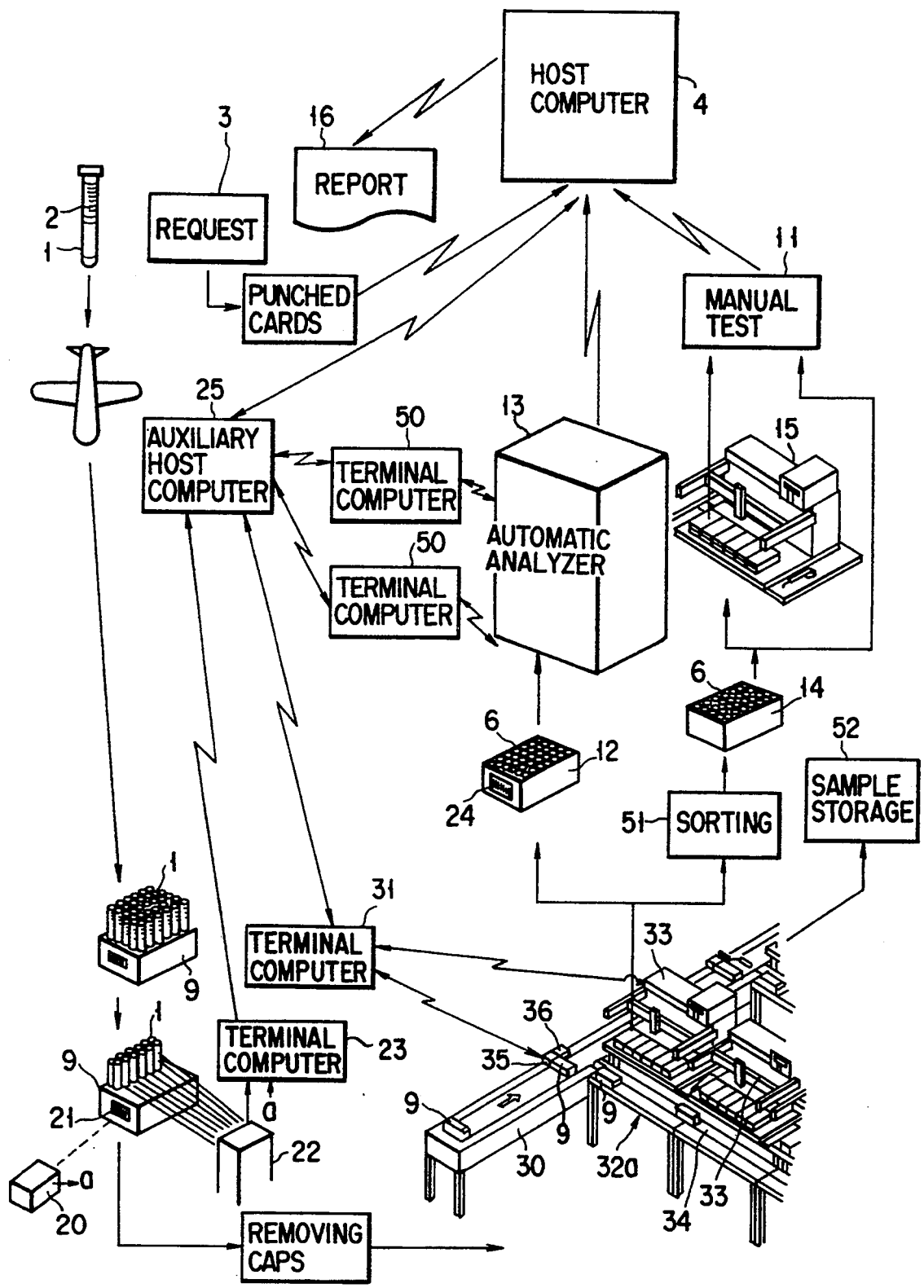
F I G. 1

AUTOMATIC CLINICAL SAMPLE DISPENSING SYSTEM

This is a division of application Ser. No. 07/913,527, filed Jul. 15, 1992 pending.

BACKGROUND OF THE INVENTION

1. Field of the Invention

The present invention relates to an automatic clinical sample dispensing method and system for dispensing a sample including a body fluid, such as blood, blood plasma, blood serum or urine, from its original container into a dispensing container to examine the sample, and a clinical sample indicating method.

2. Description of the Related Art

FIG. 7 is a flowchart for explaining a conventional clinical sample dispensing method. A label 2 showing a sample number, which is acquired by encoding information, such as patient name, test specifying information and the requester's name, into a numeral or the like, is stuck on an original container 1 (like a test tube typically 12 mm or 16 mm in diameter) containing a sample, in a hospital or the like. Then, the original container 1 is sent to a clinical laboratory, i.e., a sample test laboratory. The necessary items described on a sample test request sheet 3 are input into a host computer 4 in the sample test laboratory, by use of, for example, punched cards or keyboards. The host computer 4 prepares a list 5 of sample numbers of dispensing containers 6 which are set on dispensing container racks 12 and 14. Based on the list 5, a laboratory technologist, i.e., a worker or tester 8 stores the correlation between the coordinates of the original containers 1 in an original container rack 9 and those of the dispensing containers 6 in the dispensing container rack 12 into a memory of an automatic dispensing machine (not shown), and dispenses samples from the original containers 1 set in the original container rack 9 into the associated dispensing containers 6. The worker 8 then sets the dispensing container rack 12 which is holding the dispensing containers 6 containing the samples, in an automatic analyzer 13. When there are samples which require manual testing denoted by number 11, these are dispensed into dispensing containers 6 in another dispensing container rack 14 for such testing. Further, precision dispensing may be conducted using an automatic precision dispensing machine 15. The results of the test are output from the host computer 4 on a report 16 which is sent to the physician, i.e., test requester.

In the prior art as described above, the dispensing destinations are specified by the worker 8, i.e., manually. Using this method, there is a possibility that the tester's hands, for example, will become contaminated by samples or some other sanitary problem will occur, samples will be spilled accidentally, or the wrong dispensing destination selected. Further, since sample dispensing is carried out according to the list 5 showing the correlation between samples and the dispensing containers 6 and prepared in advance by the computer 4, when there is any sample that cannot be dispensed for some reasons, the associated dispensing container 6 in the dispensing container rack 12 becomes empty. If there is an empty container in the dispensing container rack 12, however, an ordinary automatic analyzer 13 thereafter considers the empty container as a vacant spot, i.e., not containing a sample container. When an empty container is found in the dispensing container rack 12, the original container 1 which contains the associated sample is searched for and dispensing work is performed manually. Such dispensing failures by the automatic dispensing machine affect typically 3 to 5% of all the samples per day amounting to tens of thousands of cases, for example. Every time an empty container is found, the worker 8 must look for the associated original container, thus lowering working efficiency. In addition, as the sample number is a large number including, for example, six digits, it is not easy, and takes time, to find the original container having the sample number in question in a sample storage.

SUMMARY OF THE INVENTION

It is therefore an object of the present invention to provide an automatic sample dispensing method and system capable of accurately and efficiently dispensing samples, and to provide a sample indicating method.

To achieve above mentioned object, according to the present invention, in a sample testing system for affixing sample numbers, which are encoded information about samples, each including a body fluid, contained in a number of original containers, to the associated original containers, accepting the original containers affixed with the sample numbers, and dispensing necessary amounts of samples from the original containers into dispensing containers to which a single test item or a group of test items is assigned and testing the dispensed samples, based on test specifying information corresponding to the sample numbers affixed to the original containers, an automatic sample dispensing method comprising the steps of:

setting a plurality of original containers in each original container rack and memorizing individual sample numbers in association with pre-dispensing sample positional information including a rack number attached to each original container rack and coordinates of each original container in the original container rack; and for a dispensing container rack containing a plurality of dispensing containers to each of which at least one test item is assigned, determining whether or not a sample in each of the original containers set in the original container rack should be dispensed for the each original container set in the original container rack, using the pre-dispensing sample positional information as a key, permitting an automatic dispensing machine to dispense a to-be-dispensed sample into an associated one of the dispensing containers set in the dispensing container rack, and memorizing the sample numbers in association with post-dispensing sample positional information including of a rack number affixed to the dispensing container rack where sample-dispensed dispensing containers are set and coordinates of the dispensing containers in the dispensing container rack.

In the automatic sample dispensing method of the present invention, those dispensing containers to which different single test items are assigned and/or those dispensing containers to which a group of test items is assigned may be retained in a single dispensing container rack, and, after dispensing is completed, the dispensing containers may be sorted into second dispensing container racks for a same single test item or each group of test items, based on the post-dispensing sample positional information.

Further, in the automatic sample dispensing method according to the present invention, plural types of apparently identifiable identification means may be affixed to a label to be attached to each of the dispensing containers so that a combination of the identification means forms a given pattern with the dispensing containers set in each of the second dispensing container rack, and whether proper or improper sorting has been conducted may be determined depending on whether the given pattern has been formed.

An automatic sample dispensing system for executing the automatic sample dispensing method of the present invention, comprises:

a main line for conveying original container racks for which sample numbers have been memorized in association with the pre-dispensing sample positional information;

a plurality of dispensing lines branching from the main line;

automatic dispensing machines respectively disposed in the dispensing lines;

reading units, disposed at branching portion where the dispensing lines are separated from the main line, for reading the rack numbers of the original container racks;

determining means for determining whether a sample to be dispensed in one of the dispensing lines exists in an original container rack based on the rack number of the original container rack read by the associated reading unit; and means for, when the discrimination means has determined that there is a sample to be dispensed in an original container in an original container rack, allowing the original container rack containing the sample to be conveyed on an associated dispensing line.

In the automatic sample dispensing system of the present invention, those of the dispensing lines to be branched from the main line which dispense a large number of samples having fewer test items may be arranged upstream of the main line, and those of the dispensing lines to be branched from the main line which dispense a small number of samples for mainly manual testing having a large number of test items may be arranged downstream of the main line.

In a sample testing system of the present invention, for affixing sample numbers, which are encoded information about samples, each including a body fluid, contained in a number of original containers, to the associated original containers, accepting the original containers affixed with the sample numbers, and dispensing samples from the original containers into dispensing containers to which a single test item or a group of test items is assigned and testing the dispensed samples, based on test specifying information corresponding to the sample numbers affixed to the original containers, a sample indicating method comprising the step of:

affixing a mark, which is a sample number simplified with a regularity, to each of the original containers or the dispensing containers in addition to the sample number.

According to the method of the present invention, at the time of sample dispensing, pre-dispensing sample positional information about a target original container rack is referred to in the order of the coordinates of the original container rack, and a sample that should be dispensed in the associated dispensing container rack, if found, is dispensed in that rack. If a dispensing failure occurs due to coagulation of blood or the like, this event is memorized as a dispensing failure and sample dispensing is carried out so that there are no empty dispensing containers in the dispensing container rack.

After dispensing is completed, the step of sorting the dispensing containers into second dispensing container racks for the same single test item or groups of test items based on the post-dispensing sample positional information is mainly carried out for groups of tests that involve a large number of test items and small in quantity. In this step, those dispensing containers in which samples which will undergo such a test have been dispensed are collectively set in the second dispensing container rack.

When the dispensing containers are sorted in the second dispensing container rack, the work of affixing plural types of clearly identifiable identification means to a label to be stuck on each dispensing container for confirmation of correct sorting is conducted by determining whether or not such identification means should be affixed on those sample-dispensed dispensing containers through predetermined arithmetic operations.

According to the system of the present invention, it is determined whether or not an original container rack should be transferred to a dispensing line from the main line, i.e., it is determined whether or not there is an automatic dispensing machine in the dispensing line which should dispense the sample in an original container in that original container rack, based on the sample number memorized in association with the pre-dispensing sample positional information. If there is a specified automatic dispensing machine which should dispense the sample, the original container rack is transferred from the main line to this dispensing line, while if there is no specified automatic dispensing machine which should dispense the sample, the original container rack is conveyed to downstream of the main line. The original container racks which have been used for dispensing operations are returned to the main line and are conveyed to downstream thereof.

The sample indicating method according to the present invention places a mark including a small number of characters, symbols or the like to each sample number, so that a person searching for particular samples can easily identify them.

BRIEF DESCRIPTION OF THE DRAWINGS

The features of the present invention that are believed to be novel are set forth particularity in the appended claims. The invention, together with objects and advantages thereof, may best be understood by reference to the following description of the presently preferred embodiments, together with the accompanying drawings, of which:

FIG. 1 is a structural diagram exemplifying a system that executes a method of the present invention;

DETAILED DESCRIPTION OF THE PREFERRED EMBODIMENTS

Figure 2A:
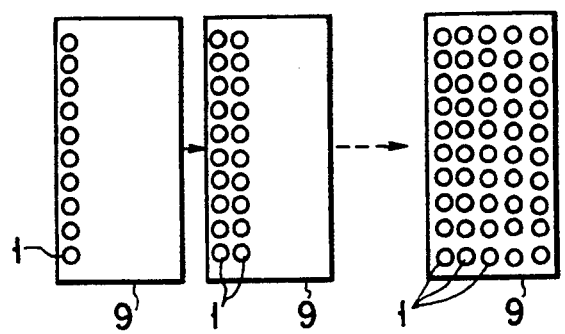
FIG. 2A is a diagram for explaining how to read a sample number of an original container to be set in an original container rack.
Figure 2B:
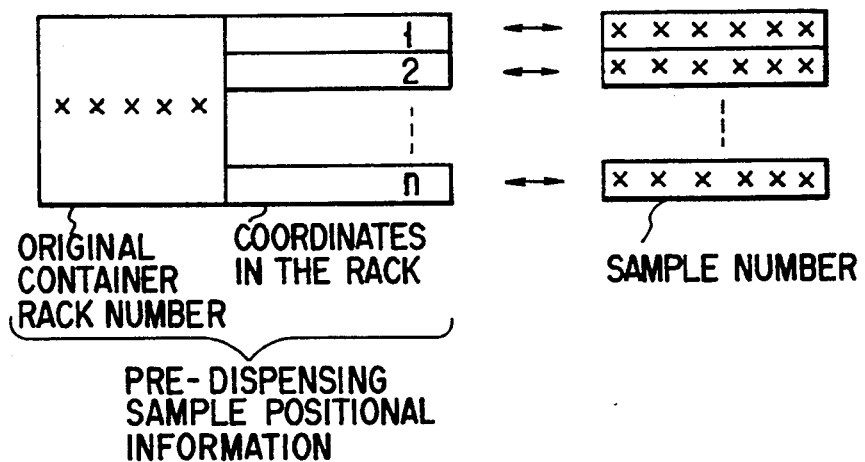
FIGS. 2B and 2C are diagrams for explaining pre-dispensing sample positional information and post-dispensing sample positional information used in the method of the present invention.
Figure 6:
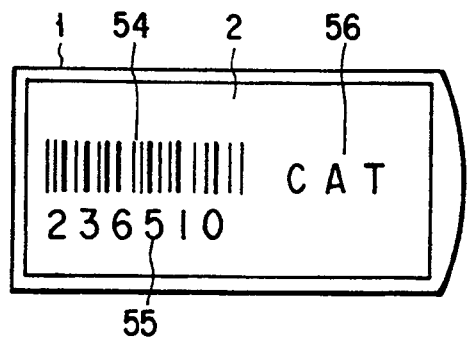
FIG. 6 is a side view of an original container showing a sample indicating method according to an embodiment of the present invention.
Figure 7:
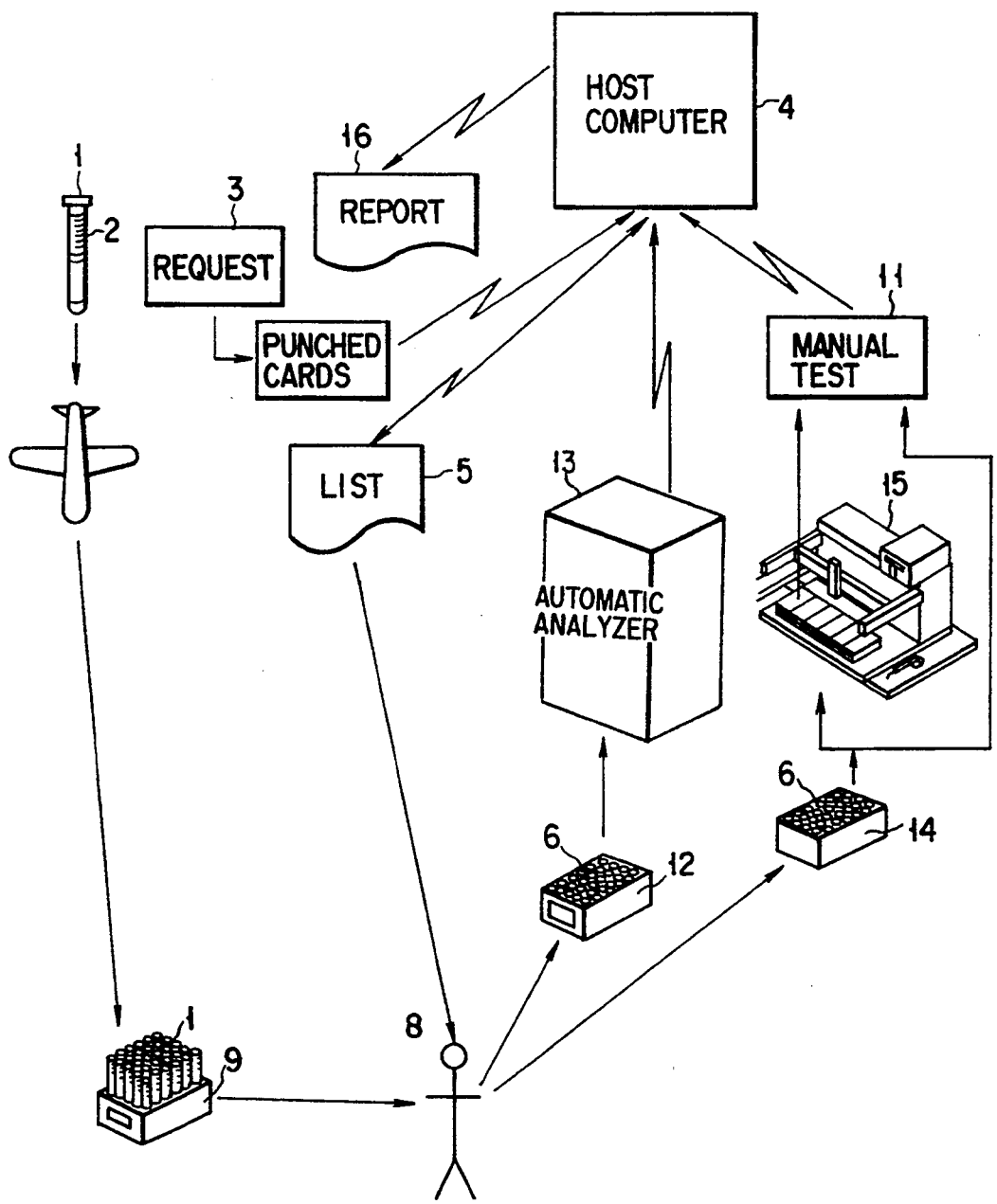
FIG. 7 is a diagram showing the structure of a conventional sample testing system.

A preferred embodiment of the present invention will now be described, with reference to the accompanying drawings. FIG. 1 shows the structure of a system that works out a sample dispensing method according to the present invention. Referring to FIG. 1, reference numeral 20 denotes an optical reader for reading an original container rack number 21 of an original container rack 9, reference numeral 22 denotes an optical reader for reading a bar-code portion of a sample number recorded on a label 2 placed on original container 9, and reference numeral 23 denotes a terminal computer for storing and transferring information read out by the optical readers 20 and 22. (The sample number includes a numeral 55 besides a bar code 54, as shown in FIG. 6.) Reading the sample numbers is executed such that the original containers 1 are placed in first column (e.g., ten containers) in the original container rack 9, and their sample numbers are automatically read by the optical reader 22, after which second column of original containers 1 are arranged and subjected to sample number reading, and so forth, until the rack becomes full (five columns in this embodiment), as shown in FIG. 2A. The terminal computer 23 transfers the sample numbers of the original containers 1 in association with pre-dispensing sample positional information, which includes of the original container rack number 21 of the original container rack 9 and their coordinates in the rack 9, to an auxiliary host computer 25, as shown in FIG. 2B. The auxiliary host computer 25, which exchanges necessary information with a host computer 4, stores the received information.

Figure 3:
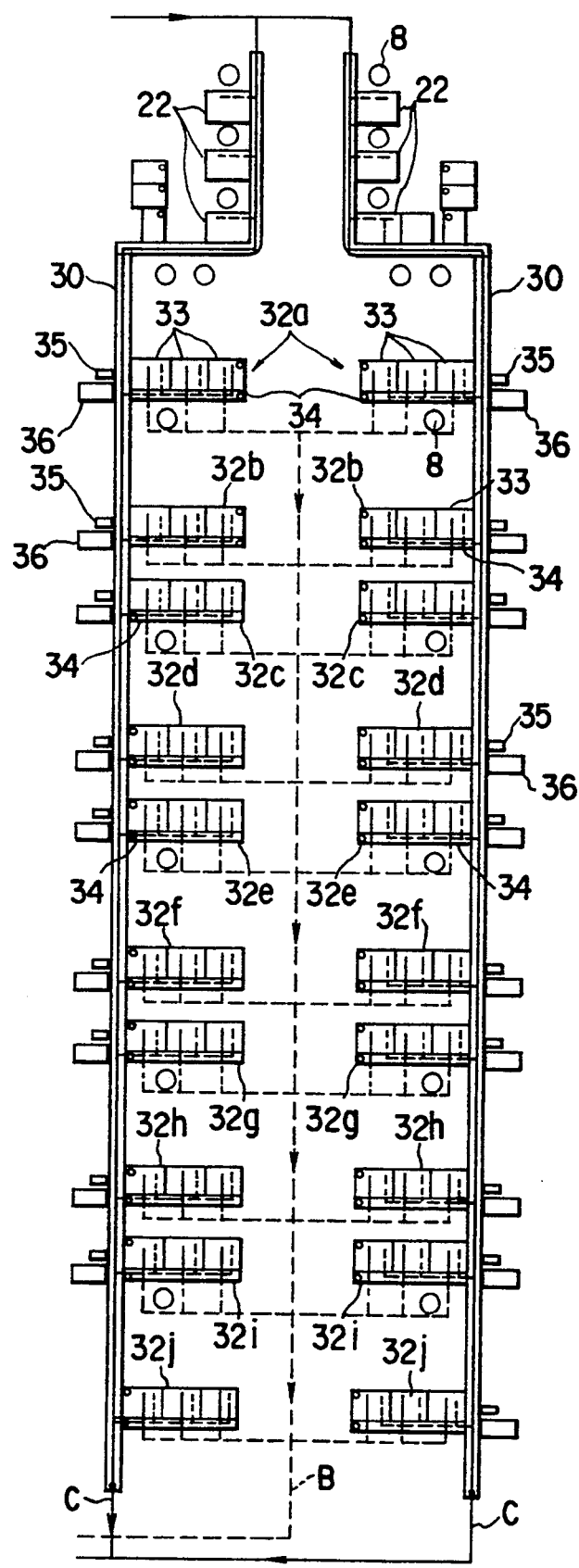
FIG. 3 is a plan view showing an automatic sample dispensing system according to an embodiment of the present invention.

As shown in FIG. 3, two main lines 30 each for conveying the original container rack 9 including the original containers 1 having undergone information reading by the above reading device are provided in consideration of possible failure. There are provided dispensing lines 32a to 32j branching from each main line 30. Each of the dispensing lines 32a-32j has automatic dispensing machines 33 (three automatic dispensing machines 33 in each dispensing line in this embodiment).

Figure 4A:
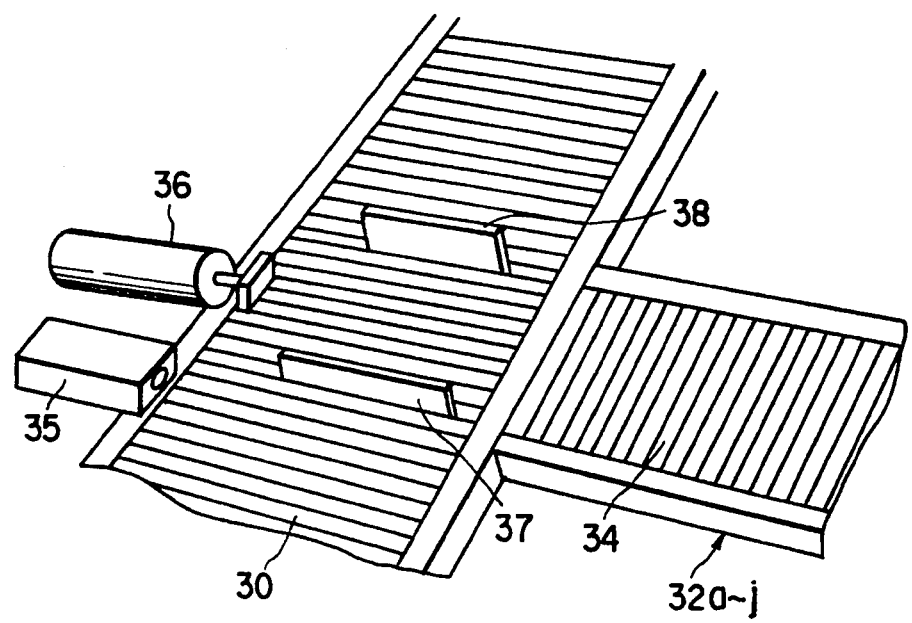
FIG. 4A is a perspective view showing the structure of a branching portion used in the system according to this embodiment.

As shown in FIG. 4A, the main line 30 comprises a roller conveyer comprising a number of rollers arranged side by side so that when they are rotated, they convey a rack placed thereon. At each branching portion of the main line 30, an optical reader 35 is provided which reads the original container rack number 21. Provided in the downstream proximity of the optical reader 35 is an air cylinder 36 serving as an actuator for feeding the original container rack 9 to the associated one of the dispensing lines 32a–32j when the original container rack 9 whose rack number 21 has been read by the optical reader 35 contains an original container 1 whose sample should be dispensed in that dispensing line. Stoppers 37 and 38 are provided in the vicinity of the optical reader 35 and air cylinder 36 on the main line 30 such that they can be urged up and down between the rollers of the main line 30 by means of, for example, air cylinders (not shown).

A terminal computer 31 is provided in each main line 30, as shown in FIG. 1. Each terminal computer 31 relays information between the auxiliary host computer 25 and the automatic dispensing machine 33, optical reader 35 and air cylinder 36 and performs line control.

In the case of each of the dispensing lines 32a-32j, samples to be dispensed are determined previously. More specifically, the dispensing lines 32a to 32c serve to dispense samples which are to be tested by an automatic analyzer for multiple biochemical items, the dispensing lines 32d to 32f serve to dispense samples which are to be tested by an automatic analyzer for another single biochemical item, and the dispensing lines 32g and 32h serve to dispense samples which are to be subjected to a special test using a radioisotope. The downstream dispensing lines 32i and 32j are provided mainly to dispense samples which are to be undergone a manual test 11, i.e., samples small in number and to be subjected to many types of tests.

In driving the air cylinder 36 based on the original container rack number 21 read by the associated optical reader 35, first, the original container rack number 21 read by the optical reader 35 is temporarily stored in the terminal computer 31. The terminal computer 31 determines whether or not samples set in the original container rack 9 are to be dispensed in the associated dispensing line, from the sample number corresponding to the pre-dispensing sample positional information of the rack 9, which has been sent from the terminal computer 23 to the auxiliary host computer 25 and stored there. If there is such a sample, the terminal computer 31 checks if that dispensing line is full. If this dispensing line is not full, the terminal computer 31 retracts the stopper 37 downward while thrusting the stopper 38 up, and feeds the original container rack 9 forward until it abuts against the stopper 38, and then protracts the air cylinder 36 to put the rack 9 on a roller conveyor 34 of the dispensing line. The worker 8 in charge of that dispensing line picks the original container rack 9 up and sets it where it should be. If the dispensing line is full and if there is another dispensing line downstream which performs the same type of sample dispensing, the original container rack 9 is to be conveyed downstream.

Figure 4B:
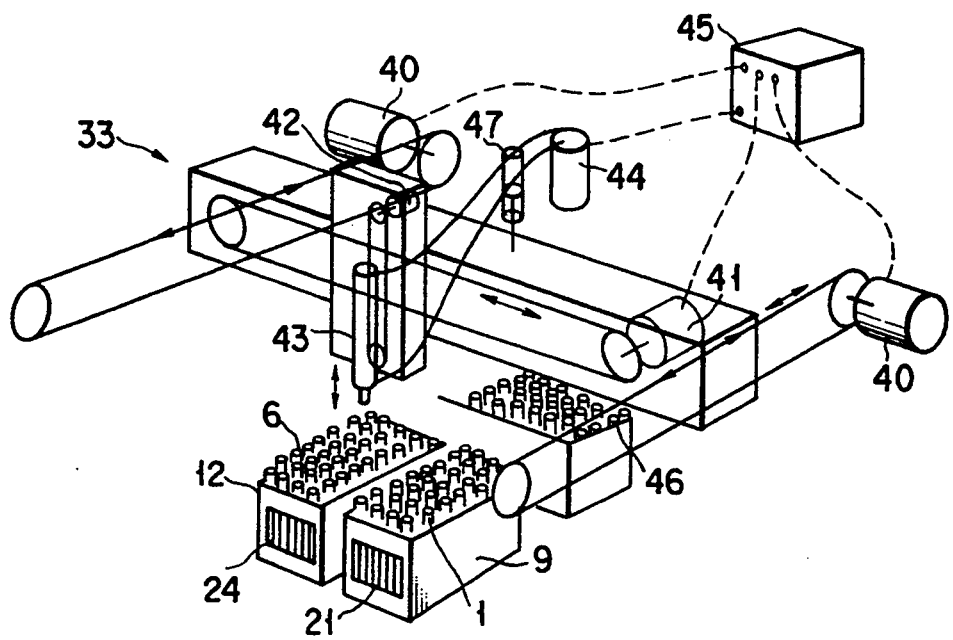
FIG. 4B is a perspective view showing the structure of an automatic dispensing machine.

FIG. 4B illustrates the structure of the automatic dispensing machine 33. The automatic dispensing machine 33 positions a dispensing nozzle 43 by means of X-axis, Y-axis and Z-axis motors 40, 41 and 42. A dispensing terminal computer 45 controls the motors 40–42 and a cylinder driving motor 44 to drive the dispensing cylinder 47 which is connected to a dispensing nozzle 43 by a plastic tube to thereby dispense a sample in an original container 1 in the original container rack 9 into an associated dispensing container 6 in a dispensing container rack 12. A straw-shaped pipe 46 is attached to the tip of the dispensing nozzle 43 to suck a sample every time of dispensing.

In dispensing a sample from the original container 1 in the original container rack 9 set in the automatic dispensing machine 33 into the associated dispensing container 6 in the dispensing container rack 12, the worker 8 allows the terminal computer 45 of the automatic dispensing machine 33 to read the rack number 21 of the original container rack 9 and the rack number 24 of the dispensing container rack 12 and then enters a key command into the terminal computer 45 to initiate sample dispensing. In response to the keyed-in command and from the sample numbers supplied from the auxiliary host computer 25, the terminal computer 45 dispenses a to-be-dispensed sample among those retained in the original containers 1 set in the original container rack 9 into the associated dispensing container 6 through the terminal computer 31 of the main line 30. When every dispensing container 6 set in the dispensing container rack 12 becomes full or is filled with a dispensed sample, the worker 8 carries out the dispensing container rack 12 in the route indicated by the broken line B in FIG. 3. (The flow of the original container rack 9 is shown by the solid line C in FIG. 3.) When there remains no samples in the original containers 1 in the original container rack 9 which should be dispensed in that dispensing line, that rack 9 is returned to the main line 30 and is then conveyed downstream.

Figure 2C:
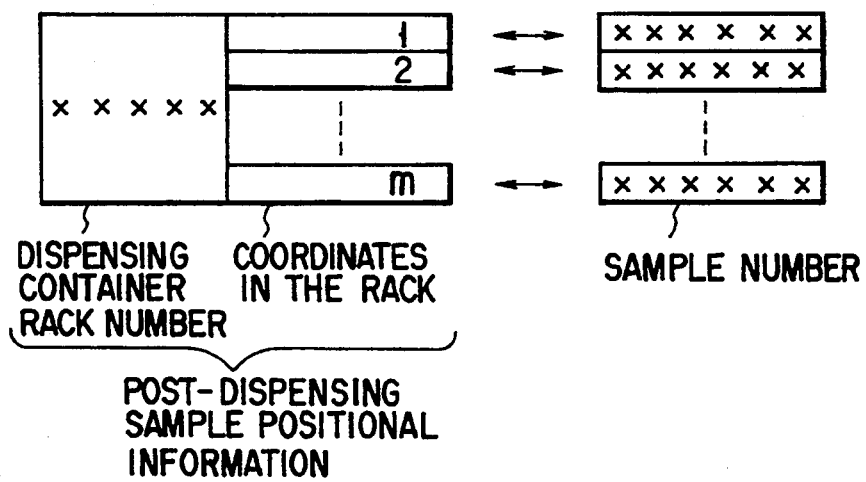

If no sample is dispensed in the target dispensing container 6 or the amount of the dispensed sample is insufficient, the event of no sample sucked up into the pipe 46 or the suction of an insufficient amount of a sample is detected by an optical sensor, which monitors the fluid level in the pipe 46, or by a state where the pressure in the cylinder 43 does not become negative. In this case, the pre-dispensing sample positional information including the original container rack number 21 and the coordinates of the original container 1 in question is stored in a dispensing failure area in the auxiliary host computer 25. Even if there is a dispensing failure, samples are put into the dispensing containers 6 in the dispensing container rack 12 in order from younger coordinates to older ones to leave no empty dispensing containers in that rack 12. When a sample is dispensed into every dispensing container 6 in each dispensing container rack 12, for that rack 12, the terminal computer 45 stores post-dispensing sample positional information including the dispensing container rack number and the coordinates therein in association with the sample numbers in the auxiliary host computer 25 through the terminal computer 31 of the main line 30, as shown in FIG. 2C.

After completion of such sample dispensing, the automatic analyzer 13 performs automatic analysis on the samples in the sample-dispensed dispensing containers 6 set in the dispensing container rack 12 under the control of each terminal computer 50. The terminal computer 50 of the automatic analyzer 13 performs analysis based on the information stored in the auxiliary host computer 25 in the above-described dispensing operation.

Figure 5A:
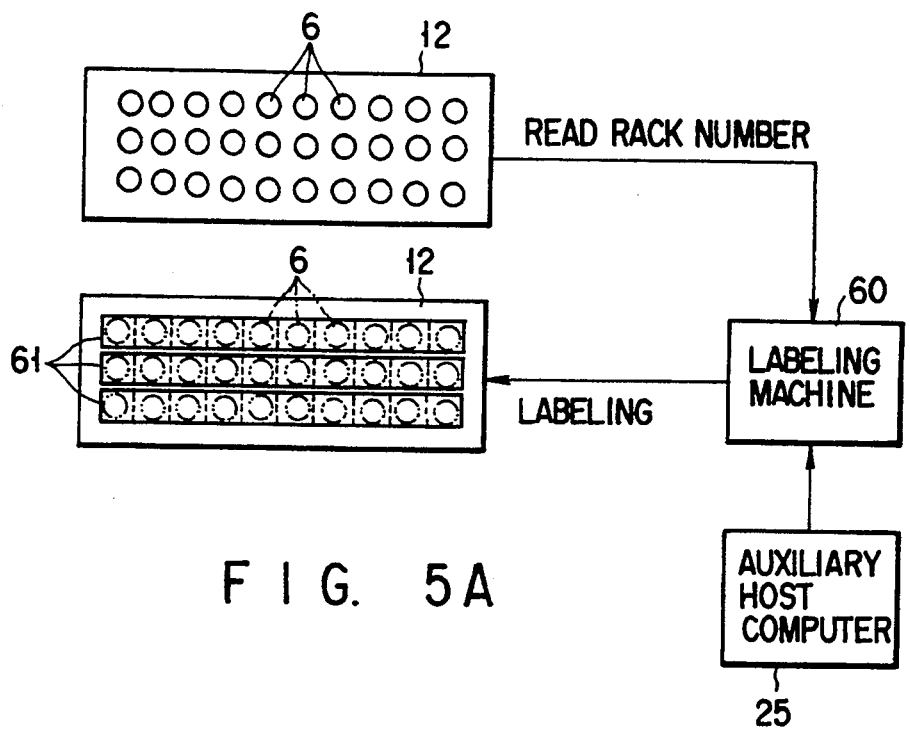
FIG. 5A is an exemplary diagram showing the labeling of dispensing containers of samples that are to be manually tested in the case of the present invention.
Figure 5B:
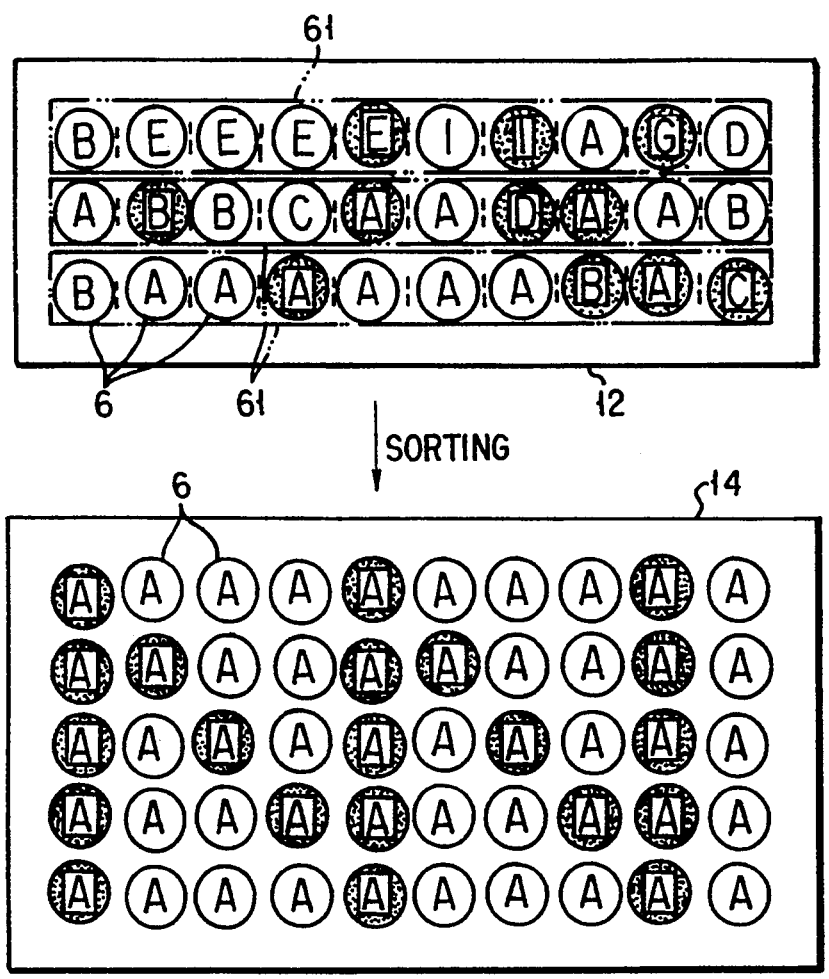
FIG. 5B is a plan view showing identification means placed on labels stuck on the top faces of the dispensing containers retained in a dispensing container rack and the arrangement of labels on dispensing containers sorted in a second dispensing container rack in the case of the present invention.

With regard to dispensing containers 6 which should undergo a manual test 11, sorting 51 which will be explained below is to be executed for each location for the manual test 11. First, as shown in FIG. 5A, a labeling machine 60 reads the rack number of the dispensing container rack 12, and puts cutable labels 61 on a column of (ten) dispensing containers 6, using a printing machine, based on the information stored in association with that rack number in the auxiliary host computer 25. The individual labels 61 may have different alphabets, A, B, C, and so forth, marked on the tops of the associated dispensing containers 6 for different types of manual testing as shown in FIG. 5B, or may have sample numbers (reception numbers assigned in order for a single test item or a group of multiple test items for that day), etc. (not shown) printed on the sides of the dispensing containers 6. The worker checks what is on the labels put on the dispensing containers 6 and sorts the dispensing containers 6 into a second dispensing container rack 14 prepared for each single test item or each group of test items.

In order to promptly determine whether or not the sorting has been done properly, the labels are colored or are affixed with identification means such as marks in such a way that a predetermined pattern is formed when the dispensing containers 6 set in the dispensing container rack 12 are sorted into the second dispensing container rack 14 prepared for each single test item or each group of test items. In FIG. 5B illustrating the second dispensing container rack for a test item A, black marks form a zigzag pattern. The affixing of the identification means may be accomplished as follows: The auxiliary host computer 25 assigns serial numbers to the samples received that day for each assigned single test item or each assigned group of test items, and sets the sample arrangement from the serial numbers in such a way that when the samples are placed in the second dispensing container rack 14, those samples which should be located at predetermined positions have colored labels. With the use of this method, when the worker sorts the dispensing containers improperly, the pattern is disturbed so that the worker can spot the wrong sorting at a glance and can correct the sorting of the samples.

For those samples which should be measured very strictly, they are accurately measured by an automatic precise dispensing machine 15 before being subjected to a manual test 11. The original container racks 9 containing samples which have been dispensed are stored at predetermined positions in a sample storage 52 for a predetermined period of time. The original container racks 9 are located in the sample storage 50 so that an operator can easily see the original rack number 21, and distinguish, and identify them by the original rack number 21.

Those samples whose dispensing by the automatic dispensing machine 33 has been failed are to be manually dispensed. For any dispensing-failed sample, therefore, the worker 8 looks for the original container 1 which contains the target sample and is stored in the sample storage 52 after being conveyed on the main line 30, and puts the sample in the automatic analyzer 13 for the required analysis or subjects it to a manual test 11. In conducting a test on such an original container 1, if the position of the original container rack 9 in the sample storage 50 and coordinates of each original container 1 in the original rack 9 are set equal to those specified by the pre-dispensing sample positional information, target original container 1 can be easily found. Further, if a bar code 54 and a numeral 55 as a sample number as well as a mark 56 acquired by encoding the sample number by a certain regularity are put in a label, as shown in FIG. 6, whether the found original container is correct one or not can easily be detected through the mark 56. As the mark 56, a word including alphabets, a numeral, katakana or hiragana (Japanese alphabets) or the like is preferable in view of simple indication and easy identification. The mark 56 is designed to have a certain regularity with the sample number.

It is preferable that the mark 56 should express a familiar animal or plant name, a person's name, or the like by fewer alphabets or numbers. In this embodiment, the mark 56 is indicated by no more than three alphabets, and is selected in such a way that the sample number including six digits is divided by "197", and "1" is added to the remainder, and if the resultant number is "1," "TOM" is put on the label 2 as the mark 56, if the resultant number is "2," it is "BAG," and if the resultant number is "197," it is "DOG." The worker can therefore easily and certainly identify the target sample. If the sample number is simplified by encoding in the above manner, the same code may be given to many samples. However, since the same code appears once for several hundred samples, this method is sufficient to ensure visual confirmation. Further, the samples even with the same code can eventually be confirmed as different when they are checked against their sample numbers, so that no practical problems will not arise. Although affixing such a mark 56 can apply to ordinary sample testing systems other than the sample testing system of the present invention, this measure, when used to look for dispensing-failed samples in the system of the present invention, will show its effectiveness in accurately and efficiently dispensing a group of dispensing-failed samples in the last stage. The mark 56 may be put on the dispensing container 6.

In short, according to the automatic sample dispensing method embodying the present invention, at the time of sample dispensing by an automatic dispensing machine, samples are sequentially dispensed in the dispensing containers set in the dispensing container rack in accordance with the coordinates of the containers in that rack and information on the dispensed samples is given in association with pre-dispensing sample positional information previously memorized, so that no samples will be dispensed in the wrong destinations. Even when a failure occurs in dispensing a sample in any dispensing container in the dispensing container rack in this dispensing work, the sample dispensing is carried out without leaving any empty dispensing container in that rack. Unlike in the prior art, therefore, at the time the dispensing container rack is set in the automatic analyzer, it is unnecessary to perform a time-consuming job of looking for the original containers corresponding to empty dispensing containers, thus significantly improving the dispensing efficiency.

Further, since those samples having fewer test items can be sorted after subjected to automatic dispensing, the active conditions of dispensing lines which have a small number of samples can be made to approach the active conditions of those dispensing lines having a large number of samples, ensuring efficient use of the lines.

According to the automatic sample dispensing system embodying the present invention, the original containers can be automatically fed into an automatic dispensing machine, so that the conveyance can be conducted efficiently and without requiring much labor.

Further, a number of samples are collectively dispensed at the upstream of the main line while a small number of samples mainly for manual testing are dispensed at the downstream of the main line. The dispensing lines can therefore be activated evenly in the entire system, resulting in high availability factor and eliminating the need for a large number of dispensing lines. This can reduce the line-occupying area so that an efficient system can be realized.

Furthermore, the sample indicating method according to the present invention can allow a person to quickly and easily find target samples, thus contributing to efficient sample dispensing with less labor.

The present examples and embodiments are to be considered as illustrative and not restrictive and the invention is not to be limited to the details given herein, but may be modified within the scope of the appended claims.

What is claimed is:

1. An automatic sample dispensing system, comprising:
    a main line for conveying original container racks containing a plurality of original containers for which sample numbers have been memorized in association with pre-dispensing sample positional information of said original containers in said original container racks and a rack number on each of said rack, said main line having upstream and downstream portions;
    a plurality of dispensing lines branching from said main line at branching portions thereof;
    automatic dispensing machines respectively disposed in said dispensing lines;
    reading units disposed at said branching portions for reading rack numbers of said original container racks;
    determining means fix determining whether or not a sample to be dispensed in one of said dispensing lines exists in an original container rack based on said rack number thereof read by one of said reading units at the branching portion of said one dispensing line;
    means for enabling the original container rack containing said sample to be conveyed on said one dispensing line when said determining means has determined that there is a sample to be dispensed in said original container rack; and
    means for disposing in said upstream portion of said main line, dispensing lines each for dispensing a first number of samples with each sample being subject to a second number of test items, and for disposing, in said downstream portion of said main line, dispensing lines for dispensing a third number of samples with each sample being subject to a fourth number of test items including manually tested samples, wherein the first number is greater than the third number and the second number is smaller than the fourth number.

* * * * *